United States Patent
Marissen et al.

(10) Patent No.: US 9,796,126 B2
(45) Date of Patent: Oct. 24, 2017

(54) PROCESS FOR MEDICAL COMPONENTS AND USES THEREOF

(71) Applicant: DSM IP ASSETS B.V., Heerlen (NL)

(72) Inventors: Roelof Marissen, Echt (NL); Olga Crespo-Biel, Echt (NL); Armand Wintjens, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 467 days.

(21) Appl. No.: 14/364,780

(22) PCT Filed: Dec. 14, 2012

(86) PCT No.: PCT/EP2012/075656
§ 371 (c)(1),
(2) Date: Jun. 12, 2014

(87) PCT Pub. No.: WO2013/087898
PCT Pub. Date: Jun. 20, 2013

(65) Prior Publication Data
US 2014/0343661 A1    Nov. 20, 2014

(30) Foreign Application Priority Data
Dec. 14, 2011  (EP) .................................... 11193513

(51) Int. Cl.
| | |
|---|---|
| *B29C 51/10* | (2006.01) |
| *B29C 51/00* | (2006.01) |
| *A61F 2/06* | (2013.01) |
| *B29C 61/06* | (2006.01) |
| *A61F 2/07* | (2013.01) |
| *B29K 23/00* | (2006.01) |
| *B29K 105/00* | (2006.01) |
| *B29L 23/00* | (2006.01) |
| *B29L 31/00* | (2006.01) |

(52) U.S. Cl.
CPC .............. *B29C 51/004* (2013.01); *A61F 2/06* (2013.01); *A61F 2/07* (2013.01); *B29C 51/10* (2013.01); *B29C 61/0608* (2013.01); *B29K 2023/0683* (2013.01); *B29K 2105/253* (2013.01); *B29K 2995/0049* (2013.01); *B29L 2023/00* (2013.01); *B29L 2031/7534* (2013.01)

(58) Field of Classification Search
CPC .......... A61F 2/07; B29C 61/02; B29C 61/025
See application file for complete search history.

(56) References Cited

U.S. PATENT DOCUMENTS

| | | | | |
|---|---|---|---|---|
| 4,897,902 A | * | 2/1990 | Kavesh | .................... D06C 7/02 139/420 R |
| 2003/0109919 A1 | * | 6/2003 | Gantt | ....................... A61F 2/06 623/1.35 |
| 2006/0058862 A1 | * | 3/2006 | Dong | ....................... A61F 2/06 623/1.5 |

* cited by examiner

*Primary Examiner* — Galen Hauth
(74) *Attorney, Agent, or Firm* — Nixon & Vanderhye P.C.

(57) ABSTRACT

The invention relates to a process for making a medical component such as a medical implant for example a graft or stent-graft, said medical component comprising ultra high molecular weight polyethylene (UHMWPE) fibers, a medical component obtainable by said process as well as uses of said process and medical component.

15 Claims, No Drawings

PROCESS FOR MEDICAL COMPONENTS AND USES THEREOF

This application is the U.S. national phase of International Application No. PCT/EP2012/075656 filed 14 Dec. 2012 which designated the U.S. and claims priority to EP Patent Application No. 11193513.6 filed 14 Dec. 2011, the entire contents of each of which are hereby incorporated by reference.

The invention relates to a process for making a medical component comprising ultra high molecular weight polyethylene (UHMWPE) fibers, a medical component obtainable by said process as well as uses of said process and medical component. The invention relates in particular to a process for making a medical implant such as a graft or stent-graft, a graft or stent-graft obtainable by said process as well as uses of said process, grafts or stent-grafts.

Tubular or hose-type medical components such as stents, grafts, stent-grafts, and artificial veins are employed as endoprostheses for the treatment of dysfunctions of hollow spaces or cavities in a living organism. Grafts, stent-grafts are considered as medical implants.

Stents usually comprise a wire cage and are intended as a guide rail type reinforcement or support of hollow bodies in humans or animals. A typical stent on its own has no covering, and therefore is usually just a metal mesh. Typically stents find application is vascular, gastrointestinal and urinary interventions.

Grafts are textile medical articles composed of special fibers and typically can be used for the aorta, femoral artery or in the forearm. Alternatively, coronary artery bypass graft is used for people with occluded coronary arteries, and often the saphenous vein or left internal thoracic arteries are used in this procedure.

Stent-grafts are composed of special fabric supported by a rigid construction, usually metal. The rigid construction is called stent. Stent-grafts are used primarily in endovascular surgery. Stent-grafts are used to support weak points in arteries, such a point commonly known as an aneurysm. Stent-grafts are most commonly used in the repair of an abdominal aortic aneurysm. Stent-grafts are also commonly placed within grafts and fistulas used for dialysis. These accesses can become obstructed over time, or develop aneurysms similar to other blood vessels in the body. A stent graft can be used in either situation to create an open lumen and prevent blood from flowing outside it.

US 2010/0324667 A1 discloses a composite vascular graft which incorporates bioactive agents. The graft of US 2010/0324667 A1 includes a luminal layer of ePTFE and a biodegradeable polymer layer including a bioactive agent e.g. an antimicrobial agent. The biodegradeable polymer layer is positioned on the external surface of the luminal ePTFE layer. The graft also includes a fabric layer which is positioned on the external surface of the biodegradeable layer. The graft is particularly useful as arterial-venous graft for hemodialysis procedures.

WO 2010/139340 A1 discloses a medical device comprising yarns made of shape memory material and polymer yarns, wherein the yarns made of said shape memory material have a polymer sheathing. Moreover, WO 2010/139340 A1 discloses a method for the production of the device, a method using the device and a delivery system comprising the device.

U.S. Pat. No. 4,897,902 A1 discloses ultrahigh molecular weight polyethylene fibers of high tenacity and modulus shrink at temperature in the range of 100-150° C. Fabrics and twisted multifilament yarns of these fibers are heat-shrunk or heat-set under these conditions.

EP 1522 277 A2, EP 0855170 A2, EP 1258229 A1, U.S. Pat. No. 6,984,243 B2 disclose a stent-grafts wherein the graft material comprises ultrahigh molecular weight polyethylene (UHMWPE) fibers.

Typically the process of making a graft or a stent-graft involves the construction of a textile tube composed of a fabric construction said fabric construction is the result of a number of process steps starting from the preparation of fibers or yarns, then the weaving of fibers or yarns to form fabrics and then the fabrics are being formed to a textile article e.g. a tube making a graft. In case of a stent-graft the latter is prepared by separately preparing a graft as discussed herein and a stent and then attaching the graft to the stent. In every step of the aforementioned manufacturing steps and due to mechanical stresses applied to the fibers in each of these steps, the mechanical properties of the fibers are compromised.

It is also desirable to use ultra high molecular weight polyethylene (UHMWPE) fibers in grafts or stent-grafts due to the high mechanical strength and biocompatibility of this type of fibers. However, in case of a graft composed of fabrics comprising UHMWPE fibers, the graft is rather supple forming wrinkles and crimps along its length and periphery making not only difficult its use for example in vascular interventions but also due to the existence of said wrinkles and crimps, the latter become potential sites for blood components to adhere, thus increasing the risk of forming thrombosis and subsequent restenosis. Furthermore, typically the inner surface of grafts or stent-grafts is not as smooth as desired, thus contributing further to an increased probability for thrombosis and subsequent restenosis. In addition, the replacement of other type of fibers e.g. polyester, polyethylene fibers by UHMWPE fibers is not straightforward since the making of grafts and/or stent grafts which are typically associated to small woven structures, demands high dimensional accuracy and at the same time must be defect-free. Producing grafts and/or stent grafts from UHMWPE fabrics is very difficult, because of the high strength and stiffness of UHMWPE fibres. The reason is that already existing minor geometrical "misfits" between the weaving equipment and the intended grafts and/or stent grafts cannot be readily compensated by the reduced ability of the UHMWPE fibers to strain, given their high stiffness. Moreover, due to the existence of said geometrical misfits, the high stresses being developed during the weaving process by the weaving equipment and at the same time the reduced ability of the UHMWPE fibers to relieve said stresses, it may easily cause fracture or jamming of components of the weaving equipment. Fracture or jamming of components of the weaving equipment due to reasons mentioned above becomes more probable especially in the case of manufacturing relatively small woven structures such as grafts and/or stent grafts. So typically, the obvious choice for the skilled person who intends to make grafts and/or stent grafts, it would be to use fibers of relatively low modulus e.g. polyester fibers, rather than using fibers of high modulus and strength such as for example UHMWPE fibers.

In addition, traditionally woven textile grafts or stent grafts are undesirably permeable by bodily fluids, especially blood.

It would therefore be advantageous to obtain a medical component for example a graft or a stent-graft of a predetermined shape that would have enhanced rigidity to be able to be used with ease during surgical interventions e.g., vascular interventions, have substantial mechanical strength, reduced permeability, enhanced smoothness of its inner surface and/or once formed its shape would be characterized of enhanced precision in respect to the desired end shape. Thus, such grafts or stent-grafts would ultimately open up an array of new opportunities in numerous fields of surgical interventions to the benefit of patients.

The object of the present invention is to address one or more of the problems or disadvantages identified herein. More particularly, it is the object of the invention to provide a process for making a medical component such as a medical implant e.g. a graft or stent-graft that would address some or all of the problems or disadvantages identified.

Therefore, broadly in accordance with the invention there is provided: a process for making a medical component C, said process comprising the steps of:

providing:
   i) an article A comprising a fabric assembly said fabric assembly comprising UHMWPE fibers, said article A is hollow having at least one opening which allows access to the inner surface of article A; and
   ii) a shaping member B which maintains its shape when it is subjected to heating at a temperature and for a time period as described in said process;

positioning in close proximity article A and shaping member B in such a way that at least part of the outer surface of shaping member B is surrounded by at least part of the inner surface of article A; and heat-shrinking article A by heating at least a portion of article A that is in close proximity with a portion of shaping member B at a temperature of at least 80° C. and of most 155° C. for a time sufficient to cause said portion of article A to shrink and conform to the shape of said portion of shaping member B, thus to obtain a heat-shrunk article A; and removing said heat-shrunk article A from shaping member B to obtain the medical component C which medical component C comprises said heat-shrunk article A.

The process according to the invention produces a medical component of a predetermined shape that has enhanced rigidity to be able to be used with ease during surgical interventions e.g., vascular interventions. Said medical component may furthermore have enhanced precision in respect to the desired end shape. Said medical component may also have substantial mechanical strength and/or reduced permeability and/or enhanced smoothness of its inner surface.

None of the cited prior art documents disclose a process for making a medical component including at least features such as, starting from an article comprising a fabric assembly said fabric assembly comprising UHMWPE fibers and which article is hollow having at least one opening which allows access to its inner surface; and heat-shrinking said article by heating at least a portion of said article that is in close proximity with a portion of a shaping member at a temperature of at least 80° C. and of most 155° C. for a time sufficient to cause said portion of the article to shrink and conform to the shape of said portion of the shaping member, thus to obtain a heat-shrunk article which is the medical component.

DEFINITIONS

By "article" is herein meant an individual object or item or element of a class designed to serve a purpose or perform a special function and can stand alone.

By "shaping member" is herein meant an article as defined herein wherein it is used to shape another article.

By "medical component" is herein meant an article as defined herein wherein its function is within the medical field such as a medical instrument, component combined together with other component to form part of a medical implant, or a medical implant as such like for example a graft, stent-graft.

By fabric is herein meant a manufactured assembly of interlacing fibers, filaments, and/or yarns having substantial surface (planar) area in relation to its thickness and adequate mechanical strength to give it a cohesive structure. Fabrics can be knitted or woven, but can also be produced by non-woven processes such as braiding, felting, and twisting. Fabric also includes laces, meshes, and nets. It is preferred that the fabric is woven or knitted. By "fabric assembly" is herein meant a component or end item comprising a number of parts or subassemblies such as fabrics, put together to form an article.

By "UHMWPE fibers" is herein meant ultra high molecular weight polyethylene (UHMWPE) that is a subset of the thermoplastic polyethylene and are explained in detail herein.

By "heat-shrinking" is herein meant shrinkage induced by the application of a means of heating.

By "medical implant" is herein meant a material inserted or grafted into an organ or structure of the body.

"Graft" and "stent-graft" are as detailed herein.

By vein is herein meant a blood vessel.

By "substantial mechanical strength" of medical component C is herein meant that their circumferential strength as measured according to ISO 7198 section 8.3.1 is at least 25 N/mm.

By "without substantially decreasing the circumferential strength of article A" is herein meant that in case the circumferential strength value of a heat-shrunk article A as measured according to ISO 7198 section 8.3.1 is decreased compared to the circumferential strength value of article A, the circumferential strength value of a heat-shrunk article A is within +/−15% of the circumferential strength value of article A, more preferably +/−12%, most preferably +/−10%, especially +/−8%.

Unless the context clearly indicates otherwise, as used herein plural forms of the terms herein (for example fibers, etc.) are to be construed as including the singular form and vice versa.

For all upper and lower boundaries of any parameters given herein, the boundary value is included in each range for each parameter. All combinations of minimum and maximum values of the parameters described herein may be used to define the parameter ranges for various embodiments and preferences of the invention.

Article A

Article A comprises a fabric assembly said fabric assembly comprising UHMWPE fibers. Article A is hollow having at least one opening which allows access to the inner surface of article A. Article A does not decompose when is subjected to heating at a temperature of at least 80° C. and of most 155° C. for a time period enough to cause said article A to shrink as a result of the applied heating.

The article A can come to various shapes, for example spherical, cylindrical, rectangular, ellipsoidal, conical, polygonal, cubical, regular or irregular. Preferably, article A is cylindrical. Even more preferably article A is tubular, most preferably article A is a tube with at least one opening at each end of its longitudinal axis.

Preferably, article A is a medical article. Preferably article A is a medical implant, e.g. graft, stent-graft, even more preferably article A is a graft.

Article A may comprise a shape memory material selected from the group consisting of a shape memory metal, a shape memory alloy and combinations thereof. An example of a shape memory metal alloy is nitinol (NiTi). The shape memory material can be as further detailed in WO 2010/139340, on p. 6, $2^{nd}$ paragraph. Even more preferably though, article A does not comprise a shape memory material because according to the process of the invention a one-time heat-shrinkage and the resulting reshaping, is sufficient, whilst reversibility of the thus obtained reshaping as typically occurring in shape memory alloys, is neither necessary nor even desired.

Preferably, the fabric assembly consists of UHMWPE fibers. In the context of the present invention ultra high molecular weight polyethylene (UHMWPE) is a subset of the thermoplastic polyethylene. UHMWPE is synthesized from monomers of ethylene, which are bonded together forming molecules of polyethylene that are several orders of magnitude longer than typical high-density polyethylene (HDPE). UHMWPE is processed using for example the following methods: compression molding, ram extrusion, gel spinning, sintering, and kneading. In general, HDPE molecules have between 700 and 1,800 monomer units per molecule, whereas UHMWPE molecules tend to have 35.000 to 350.000 monomers. The molecular weight of UHMWPE is typically higher than 1 million and usually in the range between 1 to 10 million g/mol. UHMWPE is a very tough material, actually being the toughest of all known thermoplastics. UHMWPE is odorless, tasteless, and non-toxic. Gel spinning is highly preferred for the manufacturing of high strength UHMWPE fibers. In gel spinning, a precisely-heated gel of UHMWPE and a spinning solvent (also known as spin solvent) are processed by an extruder through a spinneret. The extrudate is drawn through the air and then cooled. Then the extrudate is stretched before, during or after removing the spinning solvent. The end-result is a yarn with a high degree of molecular orientation, high crystallinity and therefore exceptional tensile strength. Gel spinning aims at isolating individual chain molecules in the solvent so that intermolecular entanglements are minimal. If intermolecular entanglements will not be kept to a minimum, then they are the main responsible for making a material such as UHMWPE unprocessable. In addition intermolecular entanglements can make chain orientation more difficult, lowering the mechanical strength of the final product. When UHMWPE is formed to fibers, the polymer chains can attain an extensive parallel orientation and a high level of crystallinity for example a crystallinity of up to 85%. Polymerisation of ethylene into UHMWPE was commercialized in the 1950s by Ruhrchemie AG, which changed names over the years; today UHMWPE powder materials are produced by Ticona, Braskem, and Mitsui. UHMWPE is available commercially either as consolidated forms, such as sheets or rods, and as fibers. UHMWPE powder may also be directly molded into the final shape of a product.

In the context of the present invention, UHMWPE is herein defined as a polyethylene having an intrinsic viscosity ($\eta_{intrinsic}$) of more than 5 dl/g (deciliter per gram). Intrinsic viscosity is a measure for molecular weight. The $\eta_{intrinsic}$ is determined according to method PTC-179 (Hercules Inc. Rev. Apr. 29, 1982) at 135° C. in decaline, the dissolution time being 16 hours, with DBPC as the anti-oxidant in an amount of 2 g/l (gram per liter) solution, and the viscosity at different concentrations is extrapolated to zero concentration. Because of their long molecule chains, stretched polyolefin fibers with an $\eta_{intrinsic}$ of more than 5 dl/g have very good mechanical properties, such as a high tensile strength, modulus, and energy absorption at break. More preferably, a polyethylene with an $\eta_{intrinsic}$ of more than 10 dl/g is chosen. This is because such gel-spun UHMWPE yarn offers a combination of high strength, low relative density, good hydrolysis resistance, and excellent wear properties, making it particularly suited for use in various biomedical applications, including implants. There is no a known maximum intrinsic viscosity, however it is preferred that the intrinsic viscosity is less than 40 dl/g and more preferably less than 30 dl/g as this allows for easier manufacturing of the fiber.

Preferably, the UHMWPE of the present invention is a linear polyethylene, i.e. a polyethylene with less than one side chain or branch per 100 carbon atoms, and preferably less than one side chain per 300 carbon atoms, a branch generally containing at least 1 carbon atom. Preferably, only polyethylene is present, but alternatively the polyethylene may further contain up to 5 mol % of alkenes that may or may not be copolymerized with it, such as propylene, butene, pentene, 4-methylpentene or octene. The polyethylene may further contain additives that are customary for such fibres, such as anti-oxidants, thermal stabilizers, colorants, etc., up to 15% w/w of the total weight of the polyethylene plus the additives, preferably 1-10% w/w of the total weight of the polyethylene plus the additives. The UHMWPE may further be added with a polyethylene of lower molecular weight. Preferably said low molecular weight polyethylene accounts for up to 10% w/w of the total weight of the UHMWPE and the lower molecular weight polyethylene.

Examples of commercially available ultra high molecular weight polyethylene fibers are SPECTRA® and Dyneema®. Preferably, medical grade of UHMWPE fibers such as Dyneema Putity® is to be used.

The UHMWPE fibers are preferably woven, non-woven, knitted, braided or combinations thereof. More preferably, the UHMWPE fibers are woven.

The density of fabrics in article A can be quantified with a cover factor D. This cover factor is defined as:

$$D = m\sqrt{t}$$

Here, t is the titer of the sheath yarns in tex (gram/km), m is the average number of yarns/mm, in all yarns' directions. Weaves with too low cover factors will show too high permeability. Weaves with too high cover factors will have a compromised strength and are very difficult to make. It was surpsingly found that for linear density between 10 to 25 dtex, a cover factor of at least 8 and of at most 40 was highly preferred, and more preferred was a cover factor of at least 10 and of at most 20.

Shaping Member B

Shaping member B maintains its shape when it is subjected to heating at a temperature and for a time period as described in the process according to the invention. Shaping member B does not decompose when is subjected to heating at a temperature of at least 80° C. and of most 155° C. for a time period enough to cause article A to shrink as a result of the applied heating. Reasonable dimensional fluctuations of the shaping member B during heat-shrinking of article A due to known and typically occurring phenomena such as thermal expansion or thermal contraction the extent of which is associated to the relative coefficients of the material from which shaping member B is made of, are to be considered within the scope of maintaining its shape in the present invention.

Preferably the shaping member B is made of metal, metal alloy or composite material.

The shaping member B can come to various shapes, for example spherical, cylindrical, rectangular, ellipsoidal, conical, polygonal, cubical, regular or irregular. Preferably, shaping member B is cylindrical for example a rod or a tube. Even more preferably shaping member B is a mandrel.

Preferably the shaping member B has a smooth surface where it will contact article A during the heat-shrinking process. It has surprisingly been found that when shaping member B has a smooth surface the inner surface of article A becomes smoother during the heat-shrinking of article A, thus reducing the risk for thrombosis and subsequent restenosis once the medical component C of the invention is used in a medical intervention as for example a medical implant, e.g. graft, stent-graft.

Since shaping member B is used in a process that produces a medical component, shaping member B is preferably suitable for medical applications. For example shaping member B can comprise a stent for example shaping member B is a stent, especially in case article A is a graft. Especially, in the case in which the shaping member B comprises a stent or the shaping member B is a stent then the stresses developed during the heat-shrinking may already be sufficient to fit article A to shaping member B, but optionally this fitting may be enhanced with protrusions at the outside of the stent, or with biocompatible adhesives.

In one embodiment, the shaping member B comprises at least two elements, which elements together form the shaping member B. The elements are preferably assembled inside article A before heat-treatment of article A and dismounted after heat-treatment of article A. In this way, it is possible to treat article of complex structure such as Y-shaped articles by the process according to the invention. The elements, which together form the shaping member B, may also be shaped to facilitate removal of the heat-shrunk article A from shaping member B after heat-shrinking of article A. In one embodiment, preferably at least one of the elements has a monotone increasing or decreasing size in the direction where the element is removed from heat-shrunk article A. Examples of this are shaping member B being a cylindrical bar and the elements being stubs of the cylindrical bar defined by a plane through the cylindrical bar, which plane is not parallel to the length of the bar and not orthogonal to the length of the bar. Most preferably, the plane passes through the end face of the bar, which allows for release of the tension between shaping member B and heat-shrunk article A by even a slight shift of the elements forming shaping member B and hence substantially facilitate removal of the shaping member after heat-shrinking of article A.

Medical Component C of the invention

The medical component C comprises a heat-shrunk article A, preferably medical component C is the heat-shrunk article A. It should be also understood that since article A comprises a fabric assembly said fabric assembly comprising UHMWPE fibers, obviously medical component C also comprises a fabric assembly comprising UHMWPE fibers. In the broader context of the invention article A is a precursor of medical component C.

Preferably, medical component C is a medical article, more preferably medical component C is a medical implant, e.g. graft, stent-graft, even more preferably medical component C is a graft.

In a preferred embodiment the invention provides for a medical component C obtainable by a process according to the present invention.

In a special embodiment the invention provides for a medical component C obtainable by a process according to the present invention wherein the circumferential strength as measured according to ISO 7198 section 8.3.1 for example on a Zwick z010 tensile meter, is at least 25 N/mm.

In a special embodiment the invention provides for a medical component C obtainable by a process according to the present invention wherein the longitudinal strength as measured according to ISO 7198, section 8.3.2 for example on a Zwick z010 tensile meter using additional slipping prevention e.g. rubber sheets is at least 25 N/mm.

In an especially preferred embodiment the invention provides for a medical component C obtainable by a process according to the present invention wherein: i) the circumferential strength as measured according to ISO 7198 section 8.3.1 for example on a Zwick z010 tensile meter is at least 25 N/mm and ii) the longitudinal strength as measured according to ISO 7198 section 8.3.2 for example on a Zwick z010 tensile meter is at least 25 N/mm.

A special feature of the medical component C according to the invention is the increased stiffness also referred to as rigidity as compared to article A. Particularly, it was found that the increased rigidity in some cases allowed component C to exhibit a surprising ability to support its own weight to great heights. This is also referred to as freestanding. One embodiment of the invention therefore concerns a medical component C, which medical component is freestanding to a height of at least 4 times the diameter of the medical component C, preferably the medical component is freestanding to a height of at least 5 times the diameter of the medical component, more preferably the medical component is freestanding to a height of at least 6 times the diameter of the medical component. The medical component is preferably freestanding to a height of at least 10 times the diameter of the medical component. The maximum preferred freestanding height of the medical component is 20 times the diameter of the medical component and typically, the freestanding height is less than 15 times the diameter of the medical component. In a particularly advantageous embodiment of this aspect of the invention, the medical component is a graft or an artificial vein and preferably an unsupported graft or an unsupported artificial vein. By unsupported is here meant that the graft and the vein does not contain a stent.

The Process of the Invention

The present invention provides for a process for making a medical component C, said process comprising the steps of:
  providing:
    i) an article A comprising a fabric assembly said fabric assembly comprising UHMWPE fibers, said article A is hollow having at least one opening which allows access to the inner surface of article A; and
    ii) a shaping member B which maintains its shape when it is subjected to heating at a temperature and for a time period as described in said process;
  positioning in close proximity article A and shaping member B in such a way that at least part of the outer surface of shaping member B is surrounded by at least part of the inner surface of article A; and
  heat-shrinking article A by heating at least a portion of article A that is in close proximity with a portion of shaping member B at a temperature of at least 80° C. and of most 155° C. for a time sufficient to cause said portion of article A to shrink and conform to the shape of said portion of shaping member B, thus to obtain a heat-shrunk article A; and removing said heat-shrunk article A from shaping member B to obtain the medical component C which medical component C comprises said heat-shrunk article A.

The fit between article A and shaping member B may be lose or tight, tightness is limited by the possibility to be able to position article A around shaping member B. The fit influences the later amount of shrinkage during heating. For tight fit, the shrinkage will be low, may be even down to zero and heat shrinkage then would rather be a heat setting process. Anyhow, in all cases, including the situation that may be denoted as heat setting, shrinkage stresses occur between article A and shaping member B. All those cases where shrinkage stresses occur are considered to be part of the invention. It was found to be advantageous to have a low heat shrinkage, as the shrinkage is related to decrease in strength of the heat-shrinked component. Particularly, it is preferred that the linear shrink of article A during heat shrinking is less than 5%.

A major advantage of the process according to the invention is that imperfections in the graft, such as loose loops or wrinkles from the braiding process, will be diminished during the heat shrinking process. Other types of defects, such as presence of fluff will also be reduced or integrated into the surface of the heat shrunk component. One embodiment of the invention therefore concerns use of the method according to the invention for removing or reducing the size or the number of weaving defects of a medical component C.

Furthermore, when a shaping member B with a smooth surface is utilized, then component C will have a reduced surface roughness on the inner surface of component C, which inner surface was contacted with the shaping member B during heat-shrinking of article A. Therefore, the surface roughness of the inner surface of component C is lower that the outer surface of component C. A smooth inner surface of component C may be advantageous as it is less likely that bacteria or blood will settle on a smooth surface. One aspect of the invention therefore concerns a medical component C obtainable by the process according to another aspect of the invention, wherein the Ra surface roughness is at least 10% lower on the inner surface of the component C, which inner surface was contacted with the shaping member B during heat-shrinkage of article A, as compared to an outer surface of the component C, which outer surface was not contacted with the shaping member B during heat-shrinkage. Preferably, the Ra surface roughness is at least 25% lower on the inside than the outside of component C and more preferably the Ra surface roughness is at least 50% lower on the inside than the outside of component C. The Ra surface roughness is the arithmetical mean roughness value defined in ISO 4287. Ra surface roughness is measured by cutting component C open and bonding the component C to a glass plate using a commercial epoxy adhesive. The side that is not intended for measurement is bonded to the substrate and the side to be measured faces away from the glass plate. To compare the inner surface of component C with the outer surface of component C two samples hence is needed. Then the epoxy adhesive has cured, Ra surface roughness is established as the average value of three measurements of Ra with a commercial roughness measurement equipment like the MarSurf PS1 from Mahr.

Preferably, the heat-shrinking of article A takes place at a temperature of at least 80° C., more preferably of at least 90° C., even more preferably of at least 100° C., most preferably of at least 110° C., especially of at least 120° C., for example of at least 130° C. Preferably, the heat-shrinking of article A takes place at a temperature of at most 155° C., more preferably of at most 150° C., even more preferably of at most 145° C., most preferably of at most 140° C., especially of at most 130° C., more especially of at most 120° C., most especially of at most 115° C., for example of at most 110° C.

Preferably, the heat-shrinking of article A takes place at a temperature of at least 80° C. and of most 150° C., more preferably the heat-shrinking of article A takes place at a temperature of at least 80° C. and of most 145° C., even more preferably the heat-shrinking of article A takes place at a temperature of at least 80° C. and of most 140° C., most preferably the heat-shrinking of article A takes place at a temperature of at least 80° C. and of most 135° C., especially the heat-shrinking of article A takes place at a temperature of at least 80° C. and of most 130° C., more especially the heat-shrinking of article A takes place at a temperature of at least 80° C. and of most 125° C., most especially the heat-shrinking of article A takes place at a temperature of at least 80° C. and of most 120° C., for example the heat-shrinking of article A takes place at a temperature of at least 80° C. and of most 115° C.

It is advantageous to heat-shrink article A at a temperature on the high end of temperatures used in the process of the invention because this allows enhanced smoothness of the inner surface of the medical component C and shorter process time. It is also advantageous to heat-shrink article A at a temperature of at least 80° C. and of most 145° C., especially at a temperature of at least 110° C. and of most 140° C. because this allows for a good balance of properties of medical component C whilst at the same time a heated liquid, as described herein, may be used to heat-shrink article A, thus allowing good heat-transfer and controlled temperature during the heat-shrinking of article A, without the need of specialized, typically also expensive, complementary equipment for these purposes.

Preferably, the heat-shrinking of article A takes place for a time period of from 1 min to 60 min.

Preferably, during the heat-shrinking of article A atmospheric pressure and/or reduced pressure for example vacuum is/are applied, more preferably reduced pressure is applied, most preferably vacuum is applied.

Preferably, the heat-shrinking of article A takes place in inert atmosphere for example noble gas, nitrogen, water or water vapor. More preferably, the heat-shrinking of article A takes place under atmospheric pressure and/or reduced pressure in inert atmosphere.

In another embodiment, the heat-shrinking of article A takes place in a heated liquid, said liquid is preferably water or aqueous solutions of water soluble salts. Use of a heated liquid is advantageous in the high heat capacity of a liquid as compared to a gas. This facilitates very fine tuning of the temperature and time of the heat-shrinking. Furthermore, use of a heated liquid typically reduces reaction time, since the heat-shrink temperature of article A can be realized faster due to high heat transfer rate between liquid and article A than between gas and article A. In one embodiment utilizing a heated liquid, article A is arranged on shaping member B and thereafter heating liquid is applied to the combined article A and shaping member B. In another embodiment, the combined article A and shaping member B is introduced into the heating liquid, for example by dipping for the required time into a container holding heating liquid at the desired temperature.

Preferably, the positioning of article A and shaping member B is of "female-to-male" type, article A being the 'female' and shaping member B being the 'male'.

Preferably, cooling is applied before removing said heat-shrunk article A from shaping member B to obtain the medical component C. More preferably cooling at temperatures below 80° C., more preferably below 60° C., even more preferably below 40° C., most preferably cooling at room temperature (23° C.±1° C.) is applied before removing said heat-shrunk article A from shaping member B to obtain the medical component C. Preferably, cooling takes place in a cooling bath because it was surprisingly found that heat-shrunk article A is released easier from shaping member B.

Other Aspects of the Invention

In another aspect the invention provides for a use of the process of the invention to reshape article A as the latter is defined herein.

In another embodiment, the invention provides for the use of the process of the invention to heat-shrink article A as the latter is defined herein, to either improve the circumferential strength of article A or at least without substantially decreasing the circumferential strength of article A, as the circumferential strength is measured according to ISO 7198 section 8.3.1.

Another aspect of the invention concerns use of the process of the invention for making medical components for medical applications. Examples of medical components, which may be prepared by the process are vascular prostheses, joint arthroplasty, orthopedic and spine implants, for example meniscus implants, surgical sutures, meshes for example hernia meshes, fabrics, woven or non-woven sheets, tapes, ribbons, bands, artificial joints, cables such as trauma fixation cables, sternum closure cables, prophylactic or per prosthetic cables, long bone fracture fixation cables, small bone fracture fixation cables, tube-like products for e.g. ligament replacement, endless loop products, bag-like, balloon-like products), tube-like products for e.g. ligament replacement, endless loop products, bag-like products, balloon-like products, stents, stent grafts, artificial veins, Y-shaped hollow structures, skirts for valve structures, such as heart valves and periphery valves and other medical components having a hollow structure.

In yet another embodiment the invention provides for a use of the process of the invention for making medical implants.

In a preferred embodiment the invention provides for a use of the process of the invention for making medical implants, wherein the medical implant is a graft or stent-graft.

Yet, another aspect of the invention is a graft (medical component C) according to the Examples 1 to 14.

Many other variations embodiments of the invention will be apparent to those skilled in the art and such variations are contemplated within the broad scope of the present invention.

All embodiments disclosed herein may be combined with each other and/or with preferred elements of the present invention. An individual feature or combination of features from an embodiment of the invention described herein, as well as obvious variations thereof, are combinable with or exchangeable for features of the other embodiments described herein, unless the person skilled in the art would immediately realize that the resulting embodiment is not physically feasible.

Further aspects of the invention and preferred features thereof are given in the claims herein.

The invention will now be described in detail with reference to the following non limiting examples which are by way of illustration only.

EXAMPLES

Examples According to the Invention: Examples 1-14

Fourteen grafts in the form of tubes, each of diameter slightly above 8 mm and 2 cm in length made of Dyneema Purity® 25 dTex fiber, were used as article A in Examples 1-14 (Tables 1a and 1b) to measure circumferential and longitudinal strength.

Two types of grafts according to the invention were made.

Examples 1-7, Article A

One type of graft was a plain weave with 8 yarns/mm, yarn directions at 90° angle (Examples 1-7, Table 1a). The number of yarns was measured on the tubes (article A). The cover factor for this type of graft was 12.6.

Examples 8-14, Article A

The other type of graft was a 4-4 twill weave with 12 yarns/mm in the longitudinal axis direction and 11 yarns/mm in the circumferential direction, yarn directions at 90° angle (Examples 8-14, Table 1b). The number of yarns was measured on the grafts (article A). The cover factor for this type of grafts was 18.

Example 1-14, Shaping Member B

Steel cylindrical rods, each of 8 mm in diameter and 10 cm or 50 cm in length and with a smooth surface, were used as shaping members (shaping member B in the language of the present invention) for each of the grafts of Examples 1-14.

Each graft of Examples 1-14 was positioned in close proximity to the steel cylindrical rod in such a way that at least part of each steel cylindrical rod was surrounded by the total inner surface of said graft.

Heat-shrinking of the grafts of Examples 1-14 has taken place for 5 min in an air-circulated oven, at temperatures as indicated in Tables 1a and 1b. Each graft was subjected to the indicated and constant temperature for 5 min and then removed from the oven and cooled at room temperature in air. The heat-shrunk grafts obtained upon removing the grafts from their metallic cylindrical rods, were the medical components C as defined herein.

The rigidity of the grafts of the Examples 1-14 was assessed via tactile inspection.

The smoothness of the inner surface of the grafts of the Examples 1-14 was assessed via tactile inspection and reported on a scale from 1 to 5. The rating of smoothness of the inner surface of the grafts is from 1 to 5, with 1 representing the roughest inner surface and 5 representing the smoothest inner surface. Smoothness of at least 2, preferably of at least 3 is desirable.

The circumferential strength of the grafts of the Examples 1-14 was measured according to ISO 7198 section 8.3.1 on a Zwick z010 tensile meter for the non-treated grafts as well as on the heat-shrunk grafts.

The circumferential strength is expressed in N/mm and is defined as:

$$[\text{Maximum Load at break/twice the Length}] = T_{max}/2L \quad (\text{N/mm}) \tag{1},$$

wherein L is the original length of the sample. The load is carried by the two sidewalls of the graft, so the line strength has to be defined using the double length The longitudinal strength of the grafts of the Examples 1-14 was measured according to ISO 7198, section 8.3.2 on a Zwick z010 tensile meter for the non-treated grafts as well as on the heat-shrunk grafts with a modification as explained herein. Due to the extremely low friction coefficient of the Dyneema® fibers and the enhanced slippage, proper clamping of the samples to the tensile meter was impossible. Therefore, the method described in ISO 7198, section 8.3.2 was modified as follows: rubber pads of 1 mm in thickness were placed between the clamps and the samples to improve grip.

The longitudinal strength is also expressed in N/mm (Newton/mm) and is defined as:

$$\text{Maximum Load at break/circumferential length} = T_{max}/(\pi \cdot D)(\text{N/mm}) \qquad (2),$$

wherein D is the diameter of the graft.

Example 1-14: Permeability Testing

In the case of permeability measurements fourteen grafts in the form of tubes, each of 8 mm in diameter and 40 cm in length made of Dyneema Purity® 25 dTex were used. Similarly to grafts used for circumferential and longitudinal strength tests, grafts of plain weave and grafts of 4-4 twill weave was utilized. Pieces of the grafts were placed on a steel rod of 8 mm in diameter and heat-shrunk at for 5 min at the temperatures indicated in Table 1a and 1b. Measurements to assess the permeability of the grafts were conducted on the non-treated grafts as well as on the heat-shrunk grafts as follows: The grafts (40 cm in length and 8 mm in diameter) were cleaned ultrasonically in water prior to testing. Subsequently, the grafts were closed at one end and suspended at a sidewall location such that the closed end is positioned at the lower side and the open end of the grafts was positioned at the top. After this, distilled water was being injected into the grafts from their open end with the help of syringe. The filling of the grafts with water was continued until a first water droplet was observed at the closed (lower) end of the graft. The height of the water column present in the graft at the point in time where the first water droplet was observed was recorded as a measure of permeability (10 cm water column is equivalent to a pressure of 1 kPa). The higher the height of the water column, the higher the pressure that needs to be applied in order the material to start leaking, subsequently the lower the permeability of said material is.

All measurements reported herein for Examples 1-14 were carried out at room temperature.

Comparative Examples: Comp. Ex 1-4

Four grafts in the form of tubes, each of 8 mm in diameter and 2 cm in length made of Dyneema Purity® 25 dTex, are used as article A in Comp. Ex 1-4 to measure circumferential and longitudinal strength.

Two types of grafts are made.

Comp Ex 1-2: Article A

One type of graft is a plain weave with 8 yarns/mm, yarn directions at 90° angle (Comp. Ex 1-2, Table 1a). The number of yarns is measured on the tubes (article A). The cover factor for this type of graft is 12.6. Article A of Comp. Ex 1-2 are hence similar to Article A of Examples 1-7.

Comp Ex 3-4: Article A

The other type of graft is a 4-4 twill weave with 12 yarns/mm in the longitudinal axis direction and 11 yarns/mm in the circumferential direction, yarn directions at 90° angle (Comp. Ex 3-4, Table 1b). The number of yarns is measured on the grafts (article A). The cover factor for this type of grafts is 18. Article A of Comp. Ex 3-4 are hence similar to Article A of Examples 8-14

Comp Ex 1-4: Shaping Member B

Steel cylindrical rods, each of 8 mm in diameter and 10 cm or 50 cm in length and with a smooth surface, are used as shaping members (shaping member B in the language of the present invention) for each of the grafts of Comp. Ex 1-4.

Each graft of Comp. Ex 1-4 is positioned in close proximity to the steel cylindrical rod in such a way that at least part of each steel cylindrical rod is surrounded by the total inner surface of said graft.

Heat-shrinking of the grafts of the Comp. Ex 1-4 is taken place for 5 min in an air-circulated oven, at temperatures as indicated in Tables 1a and 1b. Each graft is subjected to the indicated and constant temperature for 5 min and then removed from the oven and cooled at room temperature in air. The heat-shrunk grafts that are obtained upon removing the grafts from their metallic cylindrical rods are the medical components C as defined herein. Here it needs to be stressed out that in the case of Comp. Ex 2 and Comp. Ex 4 wherein the heat-shrinking of the grafts is taken place at 160° C., a medical component C is not obtained due to partial/full melting of article A during heating at 160° C. So, no measurements are performed on these grafts (medical component C).

The rigidity and smoothness of the inner surface of the grafts of the Comp. Ex 1-4 is assessed according to the way applied in the case of Examples 1-14.

The circumferential strength of the heat-shrunk grafts of the Comp. Ex 1-4 is measured according to ISO 7198 section 8.3.1 on a Zwick z010 tensile meter.

The longitudinal strength of the heat-shrunk grafts of the Comp. Ex 1-4 is measured according to ISO 7198, section 8.3.2 on a Zwick z010 tensile meter with a modification as explained herein.

In the case of permeability measurements four grafts in the form of tubes, each of 8 mm in diameter and 40 cm in length made of Dyneema Purity® 25 dTex are used. Similarly to grafts used for circumferential and longitudinal strength tests, grafts of plain weave and grafts of 4-4 twill weave was utilized. Pieces of the grafts were placed on a steel rod of 8 mm in diameter and heat-shrunk at for 5 min at the temperatures indicated in Table 1a and 1b. Measurements to assess the permeability of the heat-shrunk grafts of the Comp. Ex 1-4 is conducted according to the way described herein in the case of Examples 1-14.

All measurements reported herein for Comp. Ex 1-4, are carried out at room temperature.

TABLE 1a

| Example | Graft (article A) | | | | | | Process | Graft (medical component C) | | | | |
|---|---|---|---|---|---|---|---|---|---|---|---|---|
| | Type graft | Rigidity | Smoothness of inner surface | Permeability (Pressure [kPa] applied up to leak occurs) | Circumferential strength (N/mm) | Longitudinal strength (N/mm) | (only one feature is shown) Temperature (° C.) for heat-shrinking | Rigidity | Permeability (Pressure [kPa] applied up to leak occurs) | Smoothness of inner surface | Circumferential strength (N/mm) | Longitudinal strength (N/mm) |
| Comp. Ex 1 | plain weave | Supple | 1 | 2.5 | 71.6 | 69 | 60 | Supple | 2.5 | 1 | 71.6 | 69 |
| 1 | plain weave | Supple | | | | | 80 | Rigid | 2.8 | 2 | 71.6 | 69 |
| 2 | plain weave | Supple | | | | | 90 | Rigid | n.m. | 3 | 71.5 | n.m. |
| 3 | plain weave | Supple | | | | | 100 | Rigid | n.m. | 3 | 75.1 | n.m. |
| 4 | plain weave | Supple | | | | | 110 | Rigid | 3 | 4 | 86.3 | 65 |
| 5 | plain weave | Supple | | | | | 120 | Rigid | n.m. | 4 | 70.7 | n.m. |
| 6 | plain weave | Supple | | | | | 130 | Rigid | n.m. | 5 | 75.3 | n.m. |
| 7 | plain weave | Supple | | | | | 140 | Rigid | 3.1 | 5 | 69 | 64 |
| Comp. Ex 2 | plain weave | Supple | | | | | 160 | Medical component C is not obtained due to partial/full melting of article A during heating | | | | | n.m.: Not measured

TABLE 1b

| Example | Graft (article A) | | | | | | Process | Graft (medical component C) | | | | |
|---|---|---|---|---|---|---|---|---|---|---|---|---|
| | Type graft | Rigidity | Smoothness of inner surface | Permeability (Pressure [kPa] applied up to leak occurs) | Circumferential strength (N/mm) | Longitudinal strength (N/mm) | (only one feature is shown) Temperature (° C.) for heat-shrinking | Rigidity | Permeability (Pressure [kPa] applied up to leak occurs) | Smoothness of inner surface | Circumferential strength (N/mm) | Longitudinal strength (N/mm) |
| Comp. Ex 3 | 4-4 twill w | Supple | 1 | 2.7 | 67.9 | 37 | 60 | Supple | 2.7 | 1 | 67.9 | 37 |
| 8 | 4-4 twill w | Supple | | | | | 80 | Rigid | 3 | 2 | 65.9 | 39 |
| 9 | 4-4 twill w | Supple | | | | | 90 | Rigid | n.m. | 3 | 66.3 | n.m. |
| 10 | 4-4 twill w | Supple | | | | | 100 | Rigid | n.m. | 3 | 64.6 | n.m. |
| 11 | 4-4 twill w | Supple | | | | | 110 | Rigid | 3.1 | 3 | 60.6 | 39 |
| 12 | 4-4 twill w | Supple | | | | | 120 | Rigid | n.m. | 4 | 62.1 | n.m. |
| 13 | 4-4 twill w | Supple | | | | | 130 | Rigid | n.m. | 4 | 67.6 | n.m. |
| 14 | 4-4 twill w | Supple | | | | | 140 | Rigid | 3.1 | 5 | 61.4 | 36 |
| Comp. Ex 4 | 4-4 twill w | Supple | | | | | 160 | Medical component C is not obtained due to partial/full melting of article A during heating | | | | | n.m.: Not measured

As it can be seen from the Examples shown in Tables 1a and 1b, medical components C (grafts in the case of the Examples) that have been prepared by a process comprising the steps of:
providing:
  i) an article A comprising a fabric assembly said fabric assembly comprising UHMWPE fibers, said article A is hollow having at least one opening which allows access to the inner surface of article A; and
  ii) a shaping member B which maintains its shape when it is subjected to heating at a temperature and for a time period as described in said process;
positioning in close proximity article A and shaping member B in such a way that at least part of the outer surface of shaping member B is surrounded by at least part of the inner surface of article A; and
heat-shrinking article A by heating at least a portion of article A that is in close proximity with a portion of shaping member B at a temperature of at least 80° C. and of most 155° C. for a time sufficient to cause said portion of article A to shrink and conform to the shape of said portion of shaping member B, thus to obtain a heat-shrunk article A; and
removing said heat-shrunk article A from shaping member B to obtain the medical component C which medical component C comprises said heat-shrunk article A,
had significantly higher rigidity, lower permeability, inner surfaces of enhanced smoothness, had substantial mechanical strength whilst at the same time the circumferential strength and longitudinal strength of the grafts were not compromised by the process.

Moreover, upon visual inspection once formed the shape of each graft (medical component C) was characterized of enhanced precision in respect to the desired end shape.

Example 15: Measuring of Freestanding Height of the Grafts

The freestanding Article A from Experiment 3 and Experiment 10 as well as Component C from Experiment 3 and 10 was measured according to the following method.

The freestanding height of a graft is measured by inserting a cylindrical soft plastic tube in the fibrous tube. The wall thickness of the tube should be about 25% of the diameter of the tube. The outer diameter of the inserted tube should be about 90% of the diameter of the graft. The assembly of graft and inserted tube is then cut perpendicular to the longitudinal axis of the graft with a sharp hot knife having a temperature of 200° C. to 300° C. to obtain sections of the graft with a length of 4 times the diameter or more. Thereafter, the inserted plastic tube is removed. Using tweezers, the sections of the graft are thereafter placed with the longitudinal axis vertically on a horizontal flat surface with the cut edge in contact with the horizontal surface and after 10 seconds it is observed if the graft will stand or collapse.

For the present experiment, a tube of 7.5 mm and wall thickness of 1.8 mm was used. The hot knife had a temperature of ca. 250° C. with a cutting speed of about 2 seconds per cut. Each graft was cut into sections of 4, 5, and 6 times the diameter of the graft. Thereafter it was established if the graft sections were freestanding.

TABLE 2

| Sample | Section height | | |
|---|---|---|---|
| | 4 × diameter | 5 × diameter | 6 × diameter |
| Component C Experiment 3 (heat-shrunk) | Freestanding | Freestanding | Freestanding |
| Component C Experiment 10 (heat-shrunk) | Freestanding | Freestanding | Freestanding |
| Article A Experiment 3 (not heat-shrunk) | Not freestanding | Not freestanding | Not freestanding |
| Article A Experiment 3 (not heat-shrunk) | Not freestanding | Not freestanding | Not freestanding |

Experimental results are presented in Table 2. It was found that grafts not being subjected to the process of the invention typically will top over at a length of less than 4 times the diameter of the graft. Grafts according to the invention however typically are freestanding for length of at least 4 times the diameter of the graft and may be freestanding even up to lengths of 10 times the diameter if the process is performed under the most preferred conditions.

The large freestanding height of the grafts according to the invention allow shipping when packed in long rigid tubes without flattening, thus allowing arrival to the location where they are combined with a stent or (if no stent is connected to the graft) directly to the surgery room, still exhibiting the shape of the shaping member B and free of folds or wrinkles.

The invention claimed is:

1. A process for making a medical component C, wherein the process comprises the steps of:

a) providing:
i) an article A comprising a fabric assembly, wherein the fabric assembly comprises ultrahigh molecular weight polyethylene (UHMWPE) fibers, and wherein the article A is hollow having an inner surface and includes at least one opening which allows access to the inner surface of article A; and
ii) a shaping member B which maintains its shape when it is subjected to heating at a temperature and for a time period as described in step c);

b) positioning in close proximity article A and shaping member B in such a way that at least part of the outer surface of shaping member B is surrounded by at least part of the inner surface of article A;

c) heat-shrinking article A by heating at least a portion of article A that is in close proximity with a portion of shaping member B at a temperature of at least 110° C. and of most 140° C. for a time sufficient to cause said portion of article A to shrink and conform to the shape of said portion of shaping member B, thus to obtain a heat-shrunk article A having an inner surface that was contacted with the shaping member B during heat-shrinkage with Ra surface roughness as defined in ISO 4287 that is at least 10% lower as compared to an outer surface of the article A which was not contacted with the shaping member B during heat-shrinkage; and d) removing said heat-shrunk article A from shaping member B to obtain the medical component C comprising the heat-shrunk article A that is freestanding to a height of at least 4 times its diameter.

2. The process according to claim 1, wherein during the heat-shrinking of article A atmospheric pressure and/or reduced pressure is/are applied.

3. The process according to claim 1, wherein the fabric assembly consists of the UHMWPE fibers.

4. The process according to claim 1, wherein the fabric assembly comprising the UHMWPE fibers is selected from the group consisting of woven fabrics, non-woven fabrics, knitted fabrics, braided fabrics and combinations thereof.

5. The process s according to claim 4, wherein the fabric assembly is a woven fabric.

6. The process according to claim 1, wherein the positioning of article A and shaping member B is a positioning of female-to-male members, wherein article A is the female member, and shaping member B is the male member.

7. The process according to claim 1, wherein article A is tubular.

8. The process according to claim 7, wherein article A is a tube having a longitudinal axis with at least one opening at each end thereof.

9. The process according to claim 1, wherein article A is a medical implant.

10. The process according to claim 1, wherein article A is a graft or a stent-graft.

11. The process according to claim 1, wherein medical component C is a medical implant.

12. The process according to claim 11, wherein medical component C is a graft or a stent-graft.

13. The process according to claim 1, wherein the Ra surface roughness of the inner surface is at least 25% lower than the Ra surface roughness on the outer surface of the heat-shrunk article A.

14. The process according to claim 1, wherein the Ra surface roughness of the inner surface is at least 50% lower than the Ra surface roughness on the outer surface of the heat-shrunk article A.

15. The process according to claim 1, wherein the heat-shrunk article A is freestanding to a height of at least 5 times and less than 20 times its diameter.

\* \* \* \* \*